United States Patent
Patwardhan

(10) Patent No.: US 10,130,260 B2
(45) Date of Patent: Nov. 20, 2018

(54) MULTI-SPECTRAL TISSUE IMAGING

(71) Applicant: Canfield Scientific, Incorporated, Fairfield, NJ (US)

(72) Inventor: Sachin V. Patwardhan, Morris Plains, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 1014 days.

(21) Appl. No.: 14/465,199

(22) Filed: Aug. 21, 2014

(65) Prior Publication Data

US 2014/0364745 A1    Dec. 11, 2014

Related U.S. Application Data

(63) Continuation of application No. 12/037,154, filed on Feb. 26, 2008, now Pat. No. 8,849,380.

(60) Provisional application No. 60/990,164, filed on Nov. 26, 2007.

(51) Int. Cl.
*A61B 5/05* (2006.01)
*A61B 5/00* (2006.01)

(52) U.S. Cl.
CPC .......... *A61B 5/0071* (2013.01); *A61B 5/0059* (2013.01); *A61B 5/0064* (2013.01); *A61B 5/0075* (2013.01); *A61B 5/442* (2013.01); *A61B 5/443* (2013.01); *A61B 5/444* (2013.01); *A61B 5/445* (2013.01); *A61B 5/742* (2013.01); *A61B 2576/00* (2013.01)

(58) Field of Classification Search
None
See application file for complete search history.

(56) References Cited

U.S. PATENT DOCUMENTS

| 6,343,228 | B1 * | 1/2002 | Qu | A61B 5/0071 356/323 |
| 2002/0091324 | A1 * | 7/2002 | Kollias | A61B 5/0071 600/476 |
| 2003/0086703 | A1 * | 5/2003 | Kollias | A61B 5/442 396/14 |
| 2005/0030372 | A1 * | 2/2005 | Jung | A61B 5/0059 348/77 |

(Continued)

OTHER PUBLICATIONS

Tsumura et al. ("Independent-component analysis of skin color image", The 6th Color Imaging Conference: Color Science, Systems and Applications, vol. (6), Scottsdale, Ariz., 1998.*

*Primary Examiner* — Jonathan Cwern
(74) *Attorney, Agent, or Firm* — Brosemer, Kolefas & Assoc., LLC

(57) ABSTRACT

Apparatus and methods are disclosed for multi-spectral imaging of tissue to obtain information about the distribution of fluorophores and chromophores in the tissue. Using specific spectral bands for illumination and specific spectral bands for detection, the signal-to-noise ratio and information related to the distribution of specific fluorophores is enhanced as compared to UV photography, which uses a single RGB image. Furthermore, the chromophore distribution information derived from the multi-spectral absorption images can be used to correct the fluorescence measurements. The combined fluorescence, absorption, and broadband reflectance data can be analyzed for disease diagnosis and skin feature detection.

22 Claims, 8 Drawing Sheets

(56) References Cited

U.S. PATENT DOCUMENTS

2008/0147053 A1* 6/2008 Kang .................. A61B 5/0071
606/9

\* cited by examiner

MULTI-SPECTRAL TISSUE IMAGING

RELATED PATENT APPLICATION

The present application is a continuation of and claims the benefit under 35 U.S.C. § 120 of U.S. patent application Ser. No. 12/037,154, which was filed on Feb. 26, 2008, and issued on Sep. 30, 2014 as U.S. Pat. No. 8,849,380, and which claims priority from U.S. Provisional Patent Application No. 60/990,164, filed on Nov. 26, 2007, which is incorporated herein by reference in its entirety.

FIELD OF THE INVENTION

The present invention relates to the field of tissue imaging, and in particular, imaging the fluorescence or absorption of tissue such as skin. The present invention also relates to image processing, analysis, and segmentation, particularly as it relates to multi-spectral fluorescence and/or absorption images.

BACKGROUND INFORMATION

Light-induced fluorescence has been identified as a powerful noninvasive method for tissue pathology recognition and monitoring [1]. (Numbers in brackets refer to references listed under REFERENCES below.) A major advantage of fluorescence imaging is that fluorophores can be detected at low concentrations using harmless, non-ionizing radiation that can be applied repeatedly to the patient.

In fluorescence imaging, the energy from an external light source is absorbed and almost immediately re-emitted at a longer, lower-energy wavelength. This energy is proportional to the electronic transition from the excited state to the ground state of the fluorophore molecule. Fluorescence that originates from chromophores naturally present in the tissue (endogenous) is known as auto-fluorescence. Fluorescence emission generally depends on the fluorophore's concentration, spatial distribution throughout the tissue, local microenvironment, and light attenuation due to differences in the amount of non-fluorescing chromophores.

Endogenous fluorophores are generally associated with the structural matrix of tissue (e.g., collagen and elastin), with cellular metabolic pathways (e.g., NAD and NADH), and with proteins associated with amino acids (e.g., tryptophan, tyrosin and phenylalanine). Cells in various disease states often undergo different rates of metabolism or have different structures associated with distinct fluorescent emission spectra. Table 1 shows a list of some of the tissue fluorophores with their respective peak excitation and emission wavelengths, as well as their common applications in studying various pathological parameters [2].

TABLE 1

| Molecular source | Excitation max (nm) | Emission max (nm) | Physiologic parameter |
|---|---|---|---|
| Tryptophan | 295 | 345 | Proliferation, aging |
| Pepsin digestible collagen cross-links | 335 | 380 | Collagen cross-links, aging, glycation |
| Collagenase digestible collagen cross-links | 370 | 420 | Collagen cross-links, glycation |
| Elastin cross-links | 400 | 500 | Elastin cross-links |
| Tyrosine | 275 | 340 | Infammatory infiltrate |

TABLE 1-continued

| Molecular source | Excitation max (nm) | Emission max (nm) | Physiologic parameter |
|---|---|---|---|
| Coproporphyrin | 405 | 620 | P. acnes |
| Horn | 365 | 430 | Non-infammatory acne |
| NADH | 350 | 450 | Mitochondrial activity |

Exogenous fluorophores have been developed as disease markers, for enhancing the pathological information in fluorescence images, and for photodynamic therapy applications. The fluorescing agent is either injected into the subject's body, consumed orally or topically applied over the region of interest. A variety of endogenous reporter probes have been used for enhanced detection of early cancers, including somatostatin receptor targeted probes; folate receptor-targeted agents; tumor cell-targeted agents; agents that incorporate into areas of calcification, bone formation or both; agents activated by tumor associated proteases; and topical photodynamic therapy [3-9].

Fluorescence measurements are usually carried out in the emission mode, i.e., radiation of a single wavelength is shone onto the skin and the emitted radiation (at wavelengths longer than the excitation wavelength) is measured and can then be analyzed. The most common technique to record fluorescence within a large tissue volume is associated with illuminating the tissue with a monochromatic or narrow spectral band plane wave (expanded light beam), and then collecting fluorescence signals emitted towards a CCD camera or other types of optical detectors [6, 10]. These methods can be generally referred to as planar methods and can be applied in epi-illumination or trans-illumination mode. Planar imaging has the added advantage that the same instrumentation can be used to image fluorescence in solutions and/or excised tissues. Planar fluorescence imaging is a useful technique when probing superficial structures (<5 mm deep), for example, during endoscopy, dermatological imaging, intra-operative imaging, tissue auto-fluorescence probing, or small animal imaging [11-15], with very high throughputs (speed of imaging).

Optical properties of skin have been studied and measured by numerous investigators [16-19] using spectroscopic or diffuse reflectance techniques. Values of the absorption coefficient, scattering coefficient, and anisotropy factor for various skin layers have been published. Table 2 lists the optical properties of various skin layers and corresponding sources of data.

TABLE 2

| Skin Layer | Optical Property | Data Source |
|---|---|---|
| Stratum Corneum | Scattering Coefficient | Gemert, Jacques, Sterenborg and Star [18] |
| | Absorption Coefficient | Gemert, Jacques, Sterenborg and Star [18] |
| | Anisotropy Factor | Bruls and J. van der Leun [20] |
| Epidermis | Scattering Coefficient | Gemert, Jacques, Sterenborg and Star [18] |
| | Absorption Coefficient | Jcaques [21] |
| | Anisotropy Factor | Bruls and J. van der Leun [20] |
| Dermis | Scattering Coefficient | Gemert, Jacques, Sterenborg and Star [18] |
| | Absorption Coefficient | Cui and Ostrander and B. Lee [22] |
| | Anisotropy Factor | Jacques, Alter and Prahl [23] |

The absorption spectra of various chromophores have also been published by various researchers. Typical absorption spectra of major visible-absorbing pigments of human skin are shown in FIG. 1A. In the visible range, the main chromophores (light absorbers) of human skin are hemoglobin and melanin. Hemoglobin is found within the vascular network in the dermis while melanin is located in the epidermis. In certain skin types, like the East Asian skin type, absorption due to bilirubin is also observed. In the near-infrared (NIR) spectral range, these chromophores present very low absorption. The main light absorber in this spectral region is water.

FIG. 1B shows typical excitation/absorption spectra of the prominent endogenous fluorophores of skin, namely, collagen, elastin, flavins, NADH, porphyrins, tryptophan, pyridoxine, and lipo-pigments. FIG. 1C shows the emission spectra of the aforementioned skin endogenous fluorophores.

It should be noted that the term "porphyrin" as used herein may include porphyrin and/or its related compounds. Porphyrins are organic ring-shaped structures required in the synthesis of heme, a molecule necessary in the formation of hemoglobin. Numerous steps are involved in the pathways that result in porphyrin ring formation, and each step is dependent upon specific enzymes. Porphyrins are formed from coproporphyrin, which in turn forms pre-coproporphyrin. The *P. acnes* bacteria seems to trigger this process and all three of them (porphyrins, coproporphyrin, pre-coproporphyrin) can fluoresce, deriving their basic fluorescence capability from the porphyrin ring structure.

Diffuse optical tomography (DOT) is a means of deep-tissue optical imaging and has emerged as an important means of obtaining physiologically relevant tissue parameters such as blood oxygen saturation and total hemoglobin concentration [24]. DOT has a broad range of applications in optical breast imaging, functional brain spectroscopy and imaging, exercise medicine and photodynamic therapy monitoring [25-29]. In a typical DOT system, light is injected into tissue and is then detected at other points on the tissue surface. Three different measurement schemes are used for DOT imaging: time domain, frequency domain, and continuous wave (CW) [30-31]. Measurements are made either in transmission mode, reflection mode, or both. Of these three measurement types, the CW method is the simplest, least expensive, and provides the fastest data collection.

Fluorescence photography has been used to enhance the distribution of pigmentation, especially solar lentigenes, *Propioni bacterium acnes*, and open comedones [2, 32-35]. UV-excited fluorescence photography involves illuminating (excitation mode) the skin using a narrow-band UVA light centered at about 365 nm. The fluorescence image (emission mode) is captured using a color digital camera [2], where the camera lens is filtered so that it accepts only visible radiation (~400-700 nm). The fluorescence image obtained includes the fluorescence of coproporphyrin produced by the bacteria with a maximum emission at 620 nm (appearing red) and the fluorescence of the lesions with impacted "horn" (contained in the comedones), which fluoresce throughout the visible spectrum with a white appearance. (Note that while it is unknown which molecule or molecules within the mixture known as "horns" fluoresce, any reference herein to the fluorescence of horns is understood to include the fluorescence of any such molecule found in horns.) Both of these sources of fluorescence appear on a background of diffuse blue-green fluorescence due to the emission by the dermal collagen cross-links [2]. A similar technique is also described in the following United States Patents and Published Patent Applications: 6961517, 6922523, 6317624, 20040146290, 20050195316, 20050201935, 20050203355, 20060092315, and 20060268148. A handheld device for determining skin age, proliferation status and photo damage level based on multi-spectral measurements is described in U.S. Published Patent Application 20070004972.

In UV-excited fluorescence photography, the channels of the UVA-excited color image, (i.e., red, green and blue) can be used and analyzed individually. For example, the blue channel can be used to detect hyper-pigmented spots that cannot be seen under normal white light imaging methods. The green and red channels have been used for acne detection and monitoring.

A method of assessment for inflammatory lesions using polarized light photography, with the polarizing filters oriented perpendicularly to each other, has been demonstrated [36, 37]. Cross-polarized and parallel-polarized imaging have been used for separating surface reflectance and diffuse reflectance, or in other words, for viewing surface and subsurface information individually. Comparing the image obtained using polarized light with the image obtained using UV-excited fluorescence photography has been used for identifying inflammatory lesions.

Known UV-excited fluorescence photography techniques, however, have several drawbacks. A significant drawback of the planar imaging technique is that it cannot resolve depth and does not account for non-linear dependencies of the signal detected on propagation depth and the surrounding tissue.

Additionally, it is wrongly assumed that the camera provides the required spectral separation between the red, green and blue color bands without any overlap. The response functions of CCD imagers, which are designed based upon the human visual response to colors, exhibit massive overlap among the three color channels. It is nearly impossible to separate the spectral information from the RGB image, even by using a very accurate camera model. Without such separation, accuracy is compromised when attempting to analyze the blue, green, and red channels for collagen, horns and porphyrin fluorescence, respectively.

Furthermore, many commercially available cameras use a Bayer pattern that is designed to make the captured image look aesthetically pleasing to the viewer. In doing so, scientifically significant spectral information within the data is corrupted.

Moreover, different fluorophores have different fluorescence yields, i.e., the efficiency of producing fluorescence. Simultaneously capturing the fluorescence signal from various fluorophores will hide the information of fluorophores having lower fluorescence yields.

Furthermore, superficial fluorescence activity may reduce the contrast of underlying activity from being detected owing to the simple projection viewing.

Tissue is a heterogeneous medium and the non-uniform distribution of chromophores therein will affect the fluorescence measurement of deeper fluorophores. The fluorescence signal captured by the camera, will be influenced by absorption due to the surrounding chromophores, mainly melanin and hemoglobin.

An additional limitation of known UV-excited fluorescence photography techniques is that they do not account for the non-uniformity of the illuminating light distribution in the fluorescence measurement and subsequent analysis. The areas of a tissue that receive more illumination may produce more fluorescence from a particular fluorophore compared to the lesser illuminated areas.

Considering the fluorescence from a particular fluorophore of interest as the signal and the fluorescence from other fluorophores as the noise, the above-discussed problems of known UV-excited fluorescence photography techniques lead to poor signal-to-noise ratios in the individual R, G, and B channels of images captured using such techniques. The simultaneous capture of various fluorescence spectral bands with overlapping detector response introduces noise.

Finally, the excitation (illumination) wavelength band selected is not optimized for imaging fluorophores of interest, such as collagen, horn, and porphyrin.

There is a need, therefore, for improved techniques that address the above-discussed drawbacks of the present UV-excited fluorescence photography state of the art.

An image capture apparatus described in U.S. patent application Ser. No. 11/167,540 to Budris et al., entitled "The Programmable Multi-spectral, Image Capture Environment," and incorporated herein by reference in its entirety, provides a useful platform to target selected fluorophores and chromophores.

Patwardhan et al. have demonstrated that quantitative 3D reconstruction maps of tissue absorption and scattering can be obtained from time domain measurements [30, 38]. Using tissue simulating phantoms, Bjeorn, Patwardhan, et al., have also demonstrated the adverse effects of light absorption on fluorescence measurements and how the 3D optical property maps can be used to improve the fluorescence image quality [39].

3D reconstruction of optical properties, in particular oxy- and deoxy-hemoglobin, from multi-spectral measurements has been demonstrated on several occasions for applications such as breast cancer imaging, functional mapping of brain activity, and skin lesion imaging for melanoma [40-42].

International Patent Application PCT/US2007/063191 (WO/2007/103795) describes the use of multi-spectral imaging for demonstrating pre-emergent pimples using oxy-hemoglobin as an indicator. Various other applications of multi-spectral and/or hyper-spectral imaging are noted in U.S. Published Patent Application 20050270528. U.S. Pat. No. 6,208,749 describes a multi-spectral imaging approach for characterization of skin lesions. Further, the selection of wavelengths for multi-spectral absorption measurement can be optimized based on mathematical modeling of light/tissue interaction as demonstrated by Patwardhan et al, 2005 for multi-spectral skin lesion imaging applications [43]. 2D distribution maps of the chromophores melanin and hemoglobin have been obtained from the cross-polarized RGB images of skin using Independent Component Analysis (ICA), Principle Component Analysis (PCA), and color space transformations. 2D distribution maps of chromophores have also been obtained from multi-spectral measurements along with a mathematical model of light/tissue interaction [44-49]. Further images captured using UV and/or blue light illumination have been used to obtain distribution maps of melanin, while images captured using green light for illumination have been used to obtain distribution maps of hemoglobin.

SUMMARY OF THE INVENTION

The present invention provides apparatus and methods for capturing fluorescence and absorbance images of tissue, such as skin, using certain selected spectral wavelengths for illumination and certain selected spectral wavelengths for detection or measurement. In an exemplary embodiment, the illumination and detection wavelengths are selected using narrow-bandpass, bandpass, and/or long-pass filters. The filters are selected based on the excitation-emission spectra of fluorophores and/or the absorption spectra of chromophores of interest.

In an exemplary embodiment, the present invention features an apparatus that captures a series of fluorescence images, wherein the spectral wavelength for illumination is selected based on the excitation/absorption spectra of a certain fluorophore of interest so as to maximize the light absorption and thereby maximize the fluorescence emission signal. The same spectral wavelengths may be used to excite multiple fluorophores simultaneously if their peak emission wavelengths fall in different spectral regions and can be individually detected by proper selection of filtering in the detection path. If multiple fluorophores have overlapping excitation-emission spectra, then the wavelength corresponding to the second largest absorption peak for the fluorophore of interest may also be selected for excitation.

In a further exemplary embodiment, the present invention features an apparatus that captures a series of fluorescence images, wherein the spectral wavelengths for detection are selected based on excitation-emission spectra and the peak emission wavelengths of the fluorophores corresponding to the selected excitation wavelengths. The detection bandwidth is selected so as to capture the maximum fluorescence signal from the fluorophore of interest, while suppressing the fluorescence signals from other fluorophores.

In yet a further exemplary embodiment of the present invention, an excitation wavelength image is captured with no filter in front of the detector. As a variation, a filter may be used to block particular spectral bands from the ambient or surrounding light while allowing the spectral band of the tissue illuminating source to pass. One or more dark light images (with the illumination source turned off or blocked from reaching the detector) can be captured to estimate the dark noise of the detector.

In another exemplary embodiment of the present invention, fluorescence images are normalized for non-uniform illumination and heterogeneous absorption by the tissue, using the excitation wavelength image after subtracting the estimated dark signal from the images.

In yet another exemplary embodiment of the present invention, an apparatus captures a series of absorption images, wherein the spectral wavelength for illumination is selected based on the absorption spectrum of a chromophore of interest, such as, for example, melanin, oxy-hemoglobin, deoxy-hemoglobin, bilirubin, or water, among others, thereby enabling its isolation, detection and display.

In an exemplary embodiment of the present invention, multi-spectral absorption images are used in obtaining 2D absorption maps of individual chromophores, obtaining depth dependent information of the tissue chromophores, estimating the individual chromophore concentrations, and/or computing 3D reconstructions of the tissue absorbance due to individual chromophores.

In yet another aspect of the present invention, the chromophore absorbance, distribution, and concentration information computed from the multi-spectral absorption images is used in correcting or compensating the excitation and/or emission data or signal in fluorescence imaging.

In another embodiment of the present invention, an apparatus captures cross-polarized, parallel-polarized, and standard (white light) images of tissue. These images are used in estimating reflectance (surface and diffused), texture, roughness, and other topological characteristics of the tissue.

In yet another embodiment of the present invention, fluorescence images, absorption images, excitation images, standard (white light) images, polarized light images or any combination of these is used to detect features helpful in disease diagnosis, analysis, measurement, classification, monitoring and/or predicting the tissue condition, monitoring the effectiveness of treatment procedures or skin care/treatment products, recommending/prescribing skin care/treatment products, and displaying the feature analysis results. In doing so, various image processing, color space transformation, feature/pattern detection, and statistical techniques known in the art may be used in analyzing the images or processing some form of combined information obtained from the images.

In an exemplary embodiment of the present invention, images and/or the results of analysis may be displayed to the subject, and with or without the subject's input or feedback, may be used in the analysis, recommendation of, or treatment with an appropriate skin care product, medicine, and/or procedure.

In yet another exemplary embodiment of the present invention, the visual examination and/or processing of fluorescence and/or absorption images may be used to detect features helpful in disease diagnosis, analysis, measurement, classification, monitoring and/or predicting the skin/tissue condition, monitoring the effectiveness of skin/tissue treatment procedures and or skin care/treatment products, recommending/prescribing skin care/treatment products. A visual examination may involve looking at the illuminated tissue through an appropriate eye piece (e.g., goggles) having appropriate optical filter(s), or from the display of the captured and/or processed images.

To improve detection, classification and understanding of tissue pathologies, the present invention, in an exemplary embodiment, utilizes combined information from fluorescence images (fluorophore activity and distribution information), multi-spectral tissue absorption images (2D and/or 3D chromophore distribution/absorption maps), and broadband reflectance images, including cross-polarized, parallel-polarized, and white light images (surface and sub-surface structural and topological features).

Other aspects, features and advantages of the present invention will be apparent from the detail description of the invention and from the claims.

DETAILED DESCRIPTION

Figure 2A:
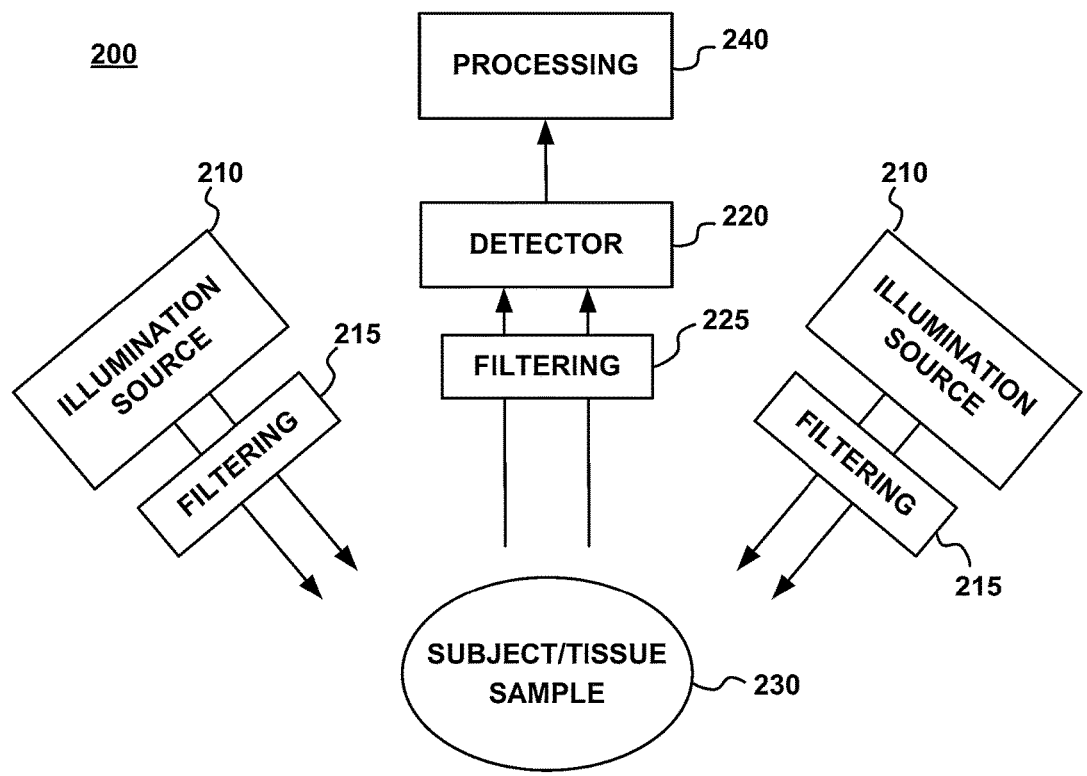
FIG. 2A is a schematic representation of an exemplary multi-spectral imaging system.

FIG. 2A schematically depicts an exemplary embodiment of a multi-spectral imaging system 200, in accordance with the present invention, for capturing images of tissue to be studied, such as skin. Illumination from one or more sources 210 is shone onto a subject's skin or a tissue sample 230 through a respective filtering element 215 and captured by a detector 220 through a filtering element 225. Each filtering element 215, 225 preferably comprises a plurality of filters, each of which can be selectively placed in the respective light path of the filtering element. (Note that the term "light" as used herein is not necessarily limited to humanly visible electromagnetic radiation, and may include portions of the electromagnetic spectrum above and below the visible range.) An exemplary embodiment of a filter wheel arrangement that may be used for filtering elements 215 and/or 225 is shown in greater detail in FIG. 2B, described below.

Preferably, the detector 220 comprises a digital camera. The detector 220 may also comprise multiple detectors, with similar or different characteristics. The information and/or images captured by the detector 220 are provided to a processing block 240 for image processing, feature detection, analysis and/or evaluation, as described in greater detail below. The processing block 240 may be implemented, for example, with one or more computers, workstations, or the like.

The exemplary system 200 is capable of capturing a variety of images, including, for example, fluorescence, absorption, excitation, polarized, white light, and/or dark light images, wherein the type of image captured depends on the filters used in the detection and illumination segments of the path of the light.

Various types of illumination sources 210 may be used in the system 200. Preferably, xenon light is used as it provides a broad spectrum from which the various illumination spectral bands can be selected using the appropriate set of optical filters. However, LASER, tunable LASER, LED, LED arrays, halogen or other types of arc lamps, among others, may be used for the various modes of illumination contemplated by the present invention. Narrow-band illumination sources such as LEDs, for example, have the advantage of not requiring optical filtering to provide illumination for a specific spectral band. For applications requiring illumination in multiple spectral bands, however, multiple illumination sources would be required.

The illumination source(s) 210 may be pulsed or left continuously on, and may employ some form of shuttering mechanism in front of it, depending upon the type of detector 220 used.

One or more illumination sources 210 may be used in the exemplary system 200 to obtain the required illumination. Preferably, two illumination sources 210 are used to provide a more uniform illumination, but depending upon the size and shape of the tissue sample or the body part of the subject to be imaged, one or more than two sources can be used. Reflectors and/or optical diffusers may also be used to obtain the desired illumination characteristics.

One or more illumination sources may also be used to provide the different modes of illumination and/or different spectral bands required as described herein, the different modes of illumination including: fluorescence, absorption, excitation, white light and polarized. Each illumination source 210 may comprise one or more illumination sources emitting in different spectral bands or modes.

Various types of optical filters may be used in the present invention for both illumination and detection. Preferably, interference filters are used because of the ease in designing and obtaining the desired optical and thermal characteristics. However, gel filters, dielectric filters, angle dependent and/or tunable filters may be used as well. Further, it is preferred to minimize the number of filters (e.g., one) used to obtain a desired spectral band in order to reduce power loss and thermal issues. A desired spectral pass-band, however, may be obtained by using a combination of two or more filters.

It is preferred that the filters used for multi-spectral imaging and other modes of illumination or detection be readily selectable, preferably under computer control, in and out of the illumination/detection light paths. This would allow for rapid filter switching and automated image capture of multiple images under multiple filtering conditions. For this purpose, in an exemplary embodiment, the various filters are mounted in filter-wheel assemblies, such as that illustrated in FIG. 2B. In the exemplary filter wheel assembly 250 of FIG. 2B, a wheel 252 includes a plurality of openings 251. A filter is arranged in at least one of the openings 251. The wheel 252 can be rotated to allow the corresponding light 'L' (i.e., illumination from a source 210 or light to a detector 220) to pass through one of the selected openings 251. The wheel 252 can be rotated about an axis 253 such as by a motor or the like under computer or user control, or it may be manually rotated. A rotary encoder or the like may be included to provide an indication, such as to a computer, of the opening 251 that is in the light path.

Figure 2B:
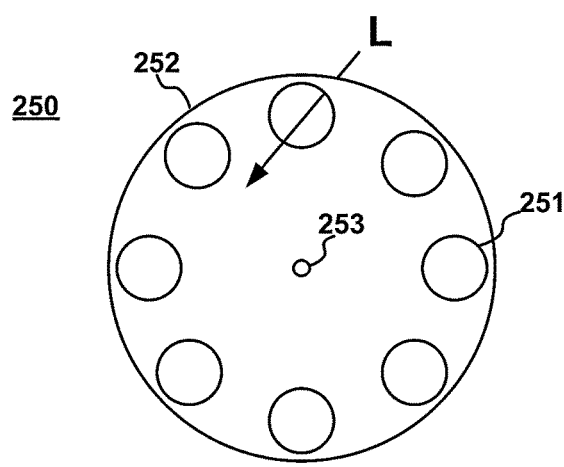
FIG. 2B illustrates an exemplary filter wheel arrangement for use in the system of FIG. 2A.

In the exemplary filter wheel assembly 250 of FIG. 2B, the filter wheel 252 includes a neutral density (ND) filter, a polarized filter, and one or more narrow-band-pass, band-pass, or long-pass filters, each centered at a wavelength $\lambda_1, \ldots, \lambda_N$. Additionally, one or more of the openings 251 of the wheel 252 may have no filter, thereby allowing light to pass through without being filtered.

A variety of arrangements for selectively inserting filtering in a light path are contemplated by the present invention, including, for example, a linear array or matrix of filters that can be moved translationally to place the selected filter in the light path.

In a further exemplary embodiment, a plurality of sources 210 are used to obtain the different modes of illumination, with the illumination from each illumination source 210 passing through a dedicated filter. In such an embodiment, the multiple images would be captured by switching the sources on or off depending on the type of image to be captured.

The methods of the present invention are independent of the order in which images are captured. Where multiple images are captured, they are preferably captured in a sequence that will optimize the overall data acquisition time, switching restrictions imposed by the illumination sources, and the filter mechanism employed. If multiple detectors are used, then the capture sequence may also be dependent on the detector parameters.

In a preferred embodiment, the detector 220 comprises a single camera due to ease in system control, low cost, and the ability to combine information from various images. Multiple cameras may be used, however, to capture different modes of images simultaneously; to capture images from various angles simultaneously; or to enable reconstruction of the three-dimensional shape of the tissue, or body part being imaged. In a further exemplary embodiment, one or cameras that can be moved to image the subject tissue from different positions can also be used. As such, three-dimensional reconstructions can be accomplished with one camera.

Various types of cameras may be used in the present invention. Digital color cameras are preferred because they allow fast and automatic image capture, easy access to the images/data in an electronic format, and enable the capture of images under all of the various modes of illumination described herein. Other types of cameras such as monochrome cameras, standard 35 mm cameras, cameras that allow instant developing film, etc., may also be used. Further, while it is preferred to capture a digital image using a camera, an array of photo-detectors (e.g., photo diodes) with or without a scanning mechanism may be used for data acquisition for all or some modes of imaging described herein.

In accordance with the present invention, it is preferred to acquire a series of images using a digital camera under the different modes of illumination. In a further exemplary embodiment, the detector 220 may comprise one or more video cameras to capture a video recording under any of the modes of illumination. The video data may be displayed on a suitable monitor (including a display monitor built into the camera) in real-time. This is desirable for comparative evaluation and/or follow-up studies to ensure proper co-registration of the images. Furthermore, the video data may be processed and the processed information may be displayed on a monitor either in real-time or after the capture.

Acquisition of images in a digital format is preferred in order to facilitate storage and post-processing. Moreover, it is preferable to use a camera that provides a "raw" output (i.e., saves images in a raw data format). It is also preferred to use the raw data format images for post-processing and analysis as it would preserve the purity of the scientific information. However, cameras that save images in other formats, such as jpeg/jpg, tiff/tif, etc may also be used for data collection. The post-processing may use the images stored in these various image formats. The images may be resized, color- and/or white-balance corrected, or converted from one format to another, including converting the "raw" images to some other format during the post-processing. Further, in an embodiment using an array of photo-detectors for image capture, the data may be post-processed before or after rendering the data as an image.

It is also possible to provide the captured image signal directly to a display device such as, for example, an eyepiece, a goggle, a monitor, or the like, thereby providing a live image.

In the present invention, it is preferred that light from the illuminating source(s) 210 falls directly (via filtering 215) onto the tissue being imaged. Also, it is preferred that the detector(s) 220 directly collect (via filtering 225) the light coming from the tissue being imaged. This kind of optical geometry provides a simple and compact configuration. However, use of indirect lighting and/or detection is possible, e.g., by using mirrors.

It is preferred to arrange the illumination sources 210 and the detector 220 in such a way that the angle formed by the source, the subject tissue, and the detector is in a range of approximately 45-50 degrees. For an angle smaller than 45-50 degrees, the penetration depth of the light into the tissue will be reduced. For an angle larger than 45-50 degrees, the amount of diffuse reflected light detected will be reduced. However, smaller or larger angles may be used for imaging due to space constraints, enhancing certain skin features, and/or enhancing the tissue surface reflectance signal over the diffuse reflectance signal and vice versa.

In a preferred exemplary embodiment of an imaging apparatus in accordance with the present invention, all or a part of the imaging apparatus is enclosed in a stationary, table-top unit (e.g., imaging booth) in order to limit the noise from ambient light and be able to capture images with the room lights on. An example of such a system is the VISIA system available from Canfield Scientific, Inc. However, images may be taken in an open environment, such as with a hand-held device, or the like, with or without ambient light.

It is also possible to observe the reflectance/fluorescence signal using some sort of an eye-piece, a goggle, a hand-held viewer, or the like. Although using a digital camera as the detector allows capturing images for further analysis and processing for feature detection, classification, and the like, and can provide a history of multiple examinations for comparison, there may be applications where such functionality may not be needed or cost considerations call for a simpler system. In an exemplary embodiment, fluorescence images may be viewed by a user, such as a physician, through a suitable viewing device. In an exemplary embodiment, the viewing device includes illumination, filtering, and magnification. Alternative embodiments may include any suitable combination of such features.

In an exemplary embodiment, the device is hand-held and includes an illumination source and a viewing window through which the physician sees the fluorescence signal. The device may or may not make contact with the skin. Further, the device preferably includes a camera mounting feature which allows mounting a camera thereon to capture the image seen in the viewing window.

Whether a closed or open implementation is used, as described above, selectable, multiple wavelength sources could be provided and one or more narrow band-pass, broad band-pass or long-pass filters may be inserted between the source and the subject as well as the detector/observer and the subject.

Image Capture and Analysis Overview

Figure 3:
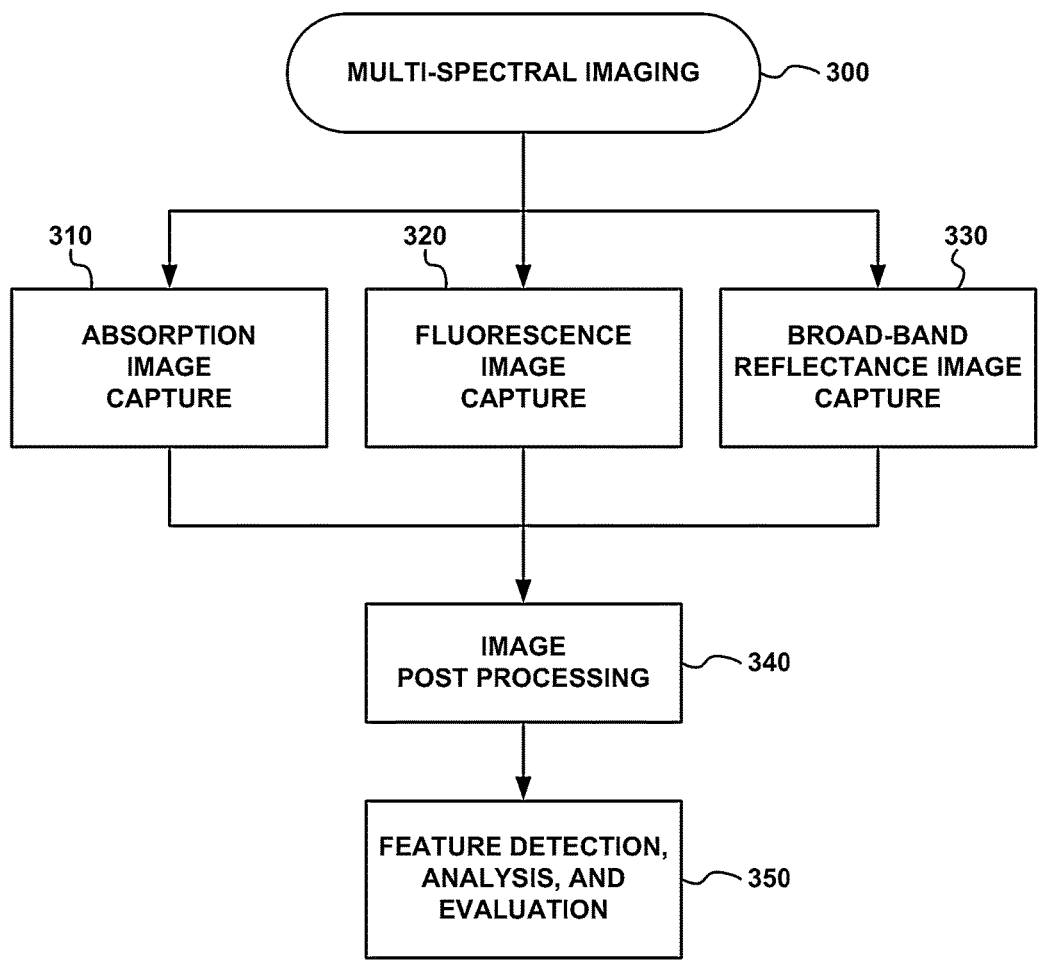
FIG. 3 is a high-level flow chart depicting an exemplary method of capturing and analyzing multi-spectral images.

FIG. 3 is a high-level flow chart providing an overview of an exemplary embodiment of a multi-spectral image capture and analysis process 300 in accordance with the present invention. The process 300 comprises an absorption image capture process 310, a fluorescence image capture process 320, and a broad-band reflectance image capture process 330. The image capture processes 310-330 are followed by image post-processing 340, and feature detection, analysis and evaluation 350. Each of the processes 310-350 is described in greater detail below.

Multi-Spectral Absorption Imaging

Figure 4:
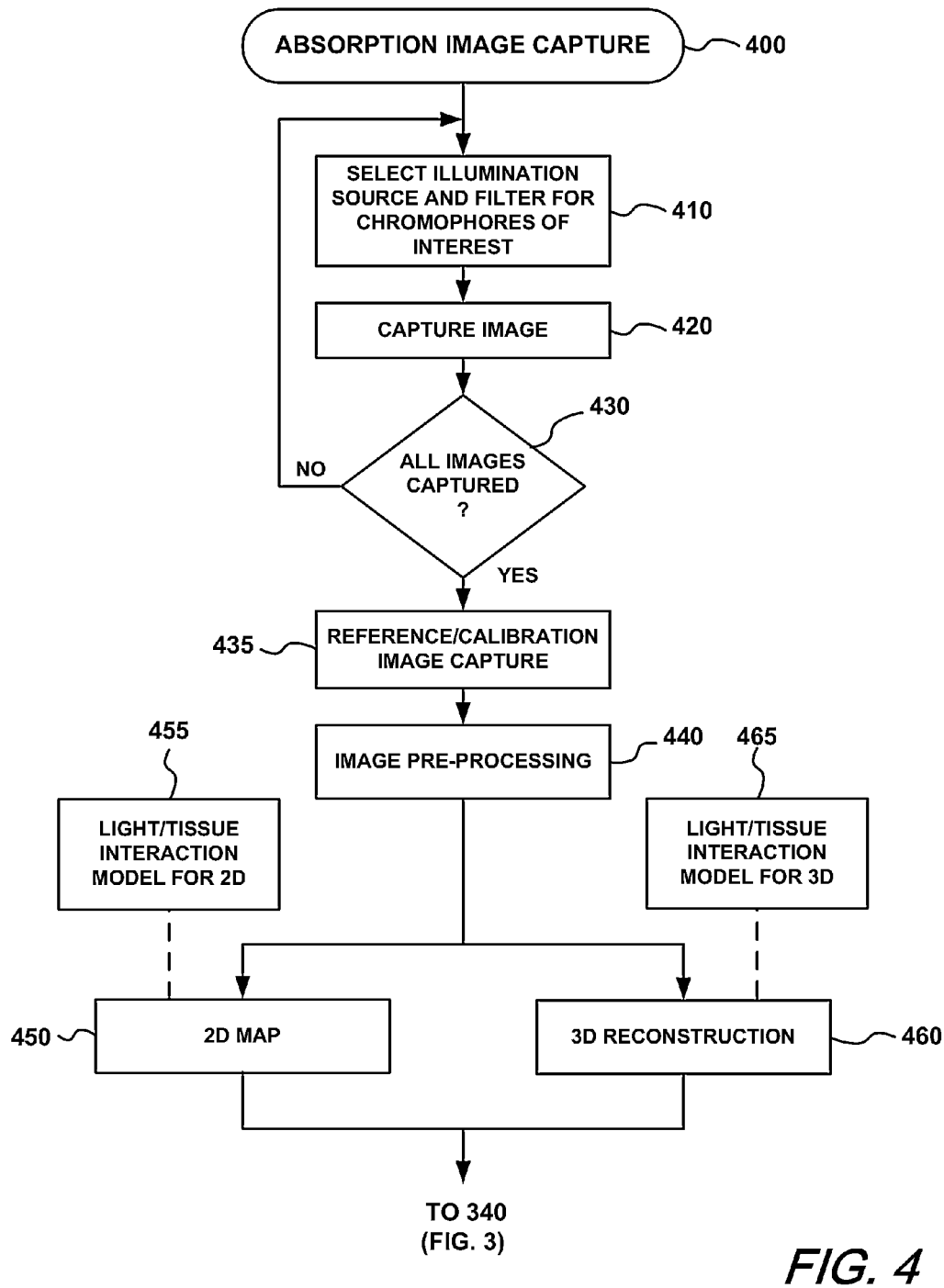
FIG. 4 is a flow chart depicting an exemplary multi-spectral fluorescence imaging method for identifying, characterizing, and measuring targeted fluorophores and/or skin features of interest.

FIG. 4 is a flow chart of an exemplary absorption image capture process 400 in accordance with the present invention. The absorption images captured can be used to obtain and analyze 2D chromophore absorption maps, perform 3D reconstruction of tissue absorption due to a particular chromophore, or correct or normalize corresponding fluorescence images. The captured images or the information derived from these images can be used, for example, in: classifying, monitoring and/or diagnosing skin/tissue conditions/diseases; making skin care or treatment recommendations; monitoring the effectiveness of skin/tissue care or treatment procedures or products; displaying feature analysis results based on the distributions of endogenous fluorophores and/or chromophores; enabling visual examination of the distributions of endogenous fluorophores and/or chromophores; evaluating skin hydration levels using water absorption information; evaluating and/or classifying skin lesions as normal, dysplastic, and/or malignant using melanin and hemoglobin absorption information; or evaluating other skin pathologies, including, for example, roseacea, hyper-pigmentation, skin burn, irritation, and inflammation, among others.

As shown in FIG. 4, the process 400 starts at 410 with selecting an illumination source and the appropriate illumination and detection filters for absorption imaging the chromophore(s) of interest (e.g., melanin, oxy-hemoglobin, deoxy-hemoglobin, water, bilirubin, etc.) As described above, it is contemplated by the present invention that absorption imaging the chromophores of interest will entail capturing a series of images under various illumination and detection conditions. The combination of illumination sources and filters selected for each image of the series is used in capturing the image at 420. Operation then proceeds to 430 in which a determination is made as to whether all of the images of the series have been captured. If not, operation loops back to 410 to select a new set of illumination sources and filters for the next image in the series.

In an exemplary method of the present invention, a series of reflectance images of the subject tissue (e.g., skin) are captured while illuminating the tissue with illumination of a narrow spectral band of approximately 10 to 40 nm (FWHM) centered at selected wavelengths in the range of 300 to 1200 nm. The apparatus of FIGS. 2A and 2B or other suitable apparatus can be used for this purpose.

In an exemplary embodiment, at least one reflectance image of the subject tissue is captured using narrow spectral band illumination centered at a wavelength of about 360 to 370 nm. In this spectral region, melanin has more absorption, while absorption due to other chromophores is less. Information about superficial melanin, sun/UV damage and spots can be obtained from this image. However, illumination in any narrow spectral band in the UVA spectral region (300 to 400 nm) may be used for this purpose.

In a further exemplary embodiment, at least one reflectance image is captured using a narrow spectral band illumination centered at a wavelength of about 450 to 460 nm. At these wavelengths absorption due to bilirubin is maximum. However, any narrow spectral band in the 400 to 500 nm spectral region may be used for this purpose.

In an exemplary method of the present invention, reflectance images of the tissue are captured using narrow spectral band illumination centered at a wavelength of about 500 to 520 nm, 530 to 550 nm, 570 to 590 nm, and/or 600 to 630 nm. These wavelengths capture the characteristics of absorption due to hemoglobin and allow isolating the oxygenated and deoxygenated hemoglobin components. The hemoglobin information can be used, for example, to evaluate erythema.

In an exemplary method of the present invention, tissue reflectance images are captured using narrow spectral band illumination centered in the red to near infrared (NIR) region (650 to 1200 nm). It is preferred that at least one image is captured in the 650 to 800 nm region because at these wavelengths, absorption due to melanin, hemoglobin, and bilirubin is very low. It is also preferred that at least one image is captured in the 800 to 1200 nm region because at these wavelengths absorption due to water is maximum. This image will have little or no information about melanin, blood, and bilirubin and hence will set a reference base line with respect to water, whose absorption will be captured in this image. (In skin optics, absorption parameters are typically defined in terms of water absorption.) This image can be used, therefore, for normalizing the measurements at other wavelengths while obtaining 2D maps of chromophore absorption. The normalization can be carried out in an image pre-processing step 440, described below.

After all absorption images of the series have been captured, as determined at 430, operation proceeds to 435 in which a reference or calibration image is captured for color, intensity, and/or white balance calibration. The purpose of this image is to act as a reference in terms of the detector response function and other instrumentation variables and is used in the pre-processing step 440 in providing data that is calibrated with respect to the detector. The detector reference image can be, for example, the reflectance image of a standard photography reference or calibration chart, such as a MacBeth chart, or of an object having a certain color or color pattern. This image may be captured during a system calibration process or during every set of measurements. In an exemplary embodiment, operation 435 can be incorporated into the image capture step 420 such as by placing color standards (e.g., a set of color chips) in the image frame during each data capture.

The various multi-spectral absorption images and reference images captured as described above are processed at a pre-processing step 440. The pre-processing 440 may include, for example, putting the captured data into a different format that can be used by the image post-processing and feature detection, analysis and detection steps (FIG. 3, 340, 350). For example, if the captured data is in the form of raw image files, in the pre-processing 440, the data is unpacked, color and white balance are applied, and it is converted into a standard image format, such as standard Red Green Blue (sRGB) that can be used by any downstream feature detection, analysis, and detection algorithms. Additionally, as mentioned above, the pre-processing 440 may include normalizing and/or calibrating the captured data with respect to tissue and/or detector reference images.

After pre-processing at 440, the image data can be used to generate, at 450, two-dimensional (2D) absorption maps of the chromophores of interest. Alternately, or additionally, a three-dimensional (3D) reconstruction can be carried out at 460.

The 2D distribution of a chromophore is obtained from a combination of multi-spectral images captured. For example, the 2D absorption map of melanin is obtained by using the combined information from images captured using illumination in the 360 to 370 nm and 650 to 1200 nm spectral bands. The image captured using the NIR illumination can be used as a reference image because the absorption due to melanin, bilirubin and hemoglobin would be negligible in this image. The 360 to 370 nm image is divided by the NIR image and the absorption map of melanin is obtained by taking a negative logarithm of this ratio.

Depth information may be derived and/or associated with the 2D maps by utilizing a light/tissue interaction model 455 for estimating the wavelength-dependent optical penetration depth of light. Such a model is described in [43].

As mentioned above, the multi-spectral images captured may also be used for obtaining 3D reconstructions of the chromophore distribution. A 3D reconstruction procedure is carried out at 460 using tomography techniques. While it is preferred to use a finite element based 3D reconstruction technique, the 3D reconstruction can also be performed using iterative techniques, such as algebraic reconstruction, finite difference based model, or analytical techniques based on diffusion or radiative transport based models that are well-known in the art.

A light/tissue interaction model 465 may be employed by the 3D reconstruction procedure for estimating the wavelength-dependent optical penetration depth of light. See, e.g., [15, 25, 30, 31, 38-43]. The 3D interaction model 465 will typically be more complex than the 2D interaction model 455 to account for the additional dimensional complexity involved.

The accuracy of applying a light-tissue interaction model to generate 3D absorption distributions depends in part on the accuracy in determining where the air-tissue boundary is. With no shape information, the tissue is typically assumed to be flat. The 3D reconstruction of absorption distributions can be improved, however, with the use of 3D shape information of the tissue being imaged. Such information can be obtained with the use of multiple detectors or a detector that can be re-positioned to take images of the tissue from different positions, as described above. With the 3D shape information thus obtained, the air-tissue boundary can be more accurately determined, thereby allowing better control over the light-tissue interaction model and more accurate 3D absorption results.

After 450 and/or 460, operation proceeds to the post-processing step 340, shown in FIG. 3.

At post-processing 340, the absorption data generated by process 400 is processed to make it usable to the feature detection, analysis, and evaluation algorithms that may follow at 350. Post-processing 340 may include, for example, normalizing captured images, combining information from one or more images or image channels, and/or applying color space transformations, among other procedures. Additionally, the 2D or 3D chromophore absorption information obtained with the process 400 can be used, at post-processing 340, to compensate or correct the fluorescence images (captured at 320) for loss of excitation and/or emission signal. A mathematical model of light/tissue interaction based upon the 2D or 3D chromophore absorption maps generated above may be used for this purpose. Advantageously, such a light/tissue interaction model is specific to the individual subject being imaged, as opposed to being based on statistical data compiled for various skin types. A method that can be used in post-processing 340 is described in [39].

Alternatively, a simpler compensation technique such as using negative logarithmic ratio data of the fluorescence image and the 2D absorption map may be used to perform the fluorescence image compensation at 340. Furthermore, in certain cases, depending upon the sources and detectors being used for imaging and the skin area of interest to be imaged, a non-uniform light distribution pattern may be used for illumination/excitation during fluorescence imaging.

Multi-Spectral Fluorescence Imaging

Figure 5:
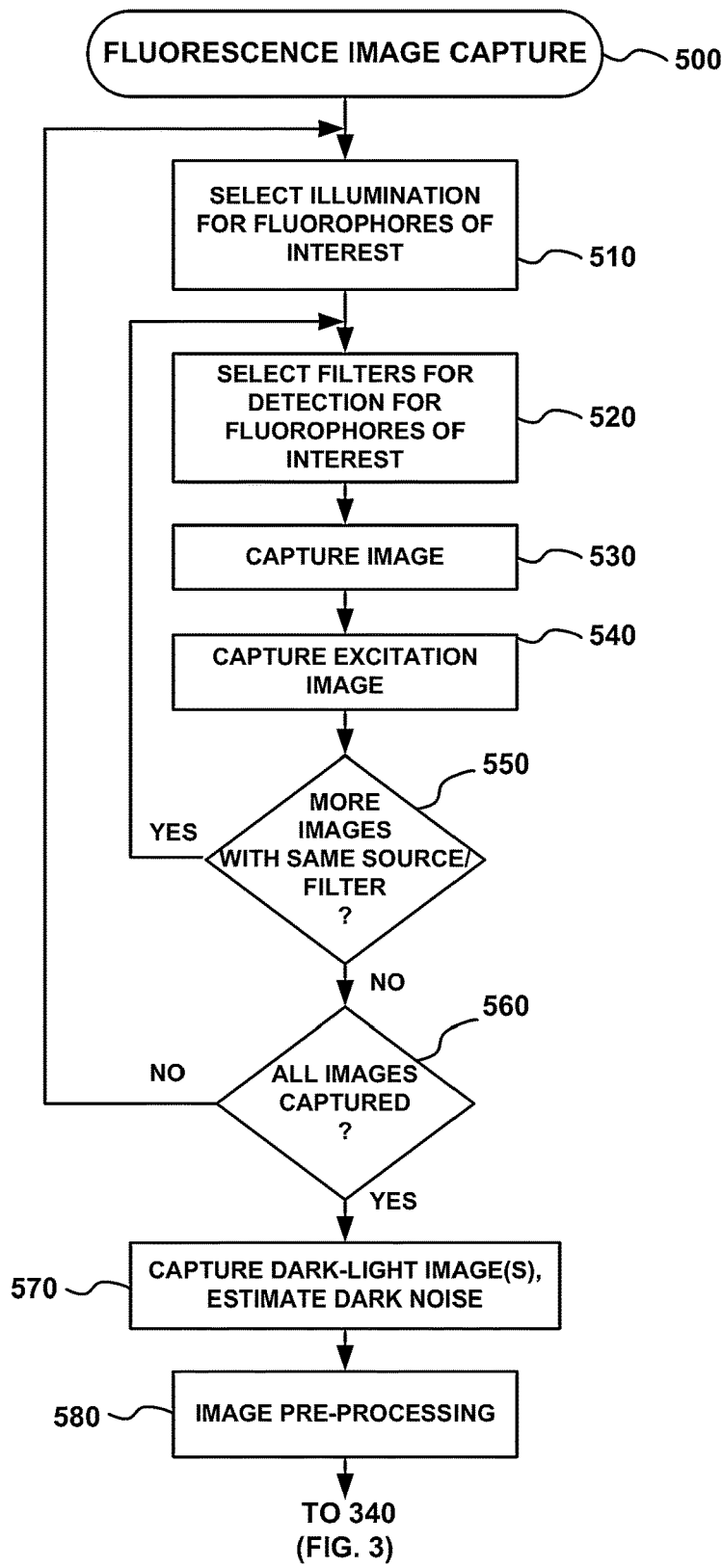
FIG. 5 is a flow chart depicting an exemplary multi-spectral absorption imaging method for identifying, characterizing, and measuring targeted chromophores and/or skin features of interest.

FIG. 5 is a flow chart of an exemplary embodiment of a fluorescence image capture process 500 in accordance with the present invention. The captured images or the information derived from these images can be used, for example, in: classifying, monitoring and/or diagnosing skin/tissue conditions or diseases; making skin care/treatment products recommendations; monitoring the effectiveness of skin/tissue treatment procedures and/or care/treatment products; displaying feature analysis results based on the distributions of endogenous fluorophores and/or chromophores; or enabling visual examination of the distributions of endogenous fluorophores and/or chromophores.

In an exemplary embodiment of a method of the present invention, a series of fluorescence images are captured under a variety of different combinations of illumination and detection filtering. Each of the series of images is captured by illuminating the subject tissue (e.g., skin) with illumination of a specific wavelength or band of wavelengths and capturing the fluorescence signal from one or fluorophores using the appropriate detection filtering. The apparatus of FIGS. 2A and 2B or other suitable apparatus can be used in carrying out the process 500.

As shown in FIG. 5, at 510, illumination is selected to provide excitation of the fluorophores of interest. As described above, with respect to the exemplary apparatus of FIGS. 2A and 2B, this entails selecting an appropriate illumination source and/or corresponding illumination filtering. For example, for acne and other skin pathology related imaging applications where the fluorescence signal from collagen, porphyrin, and horns is to be measured, illumination of a narrow spectral band of approximately 20 to 40 nm (FWHM) centered around 405 nm (±15 nm) can be used. At this excitation wavelength, the fluorescence emission from porphyrin is maximum, owing to its maximum absorption; the fluorescence signal of collagen can be readily separated from NADH; and a sufficient emission signal from horns can be obtained. However, any narrow band of spectral wavelengths from 330 nm to 430 nm can be used for imaging these fluorophores with an associated signal-to-noise ratio trade-off. For example, a narrow spectral band of approximately 20 to 40 nm (FWHM) centered around 360 to 370 nm may be used for illumination because at these wavelengths, the absorption of light by collagen is maximum while sufficient fluorescence signals can be obtained from horns and porphyrin.

Figure 1A:
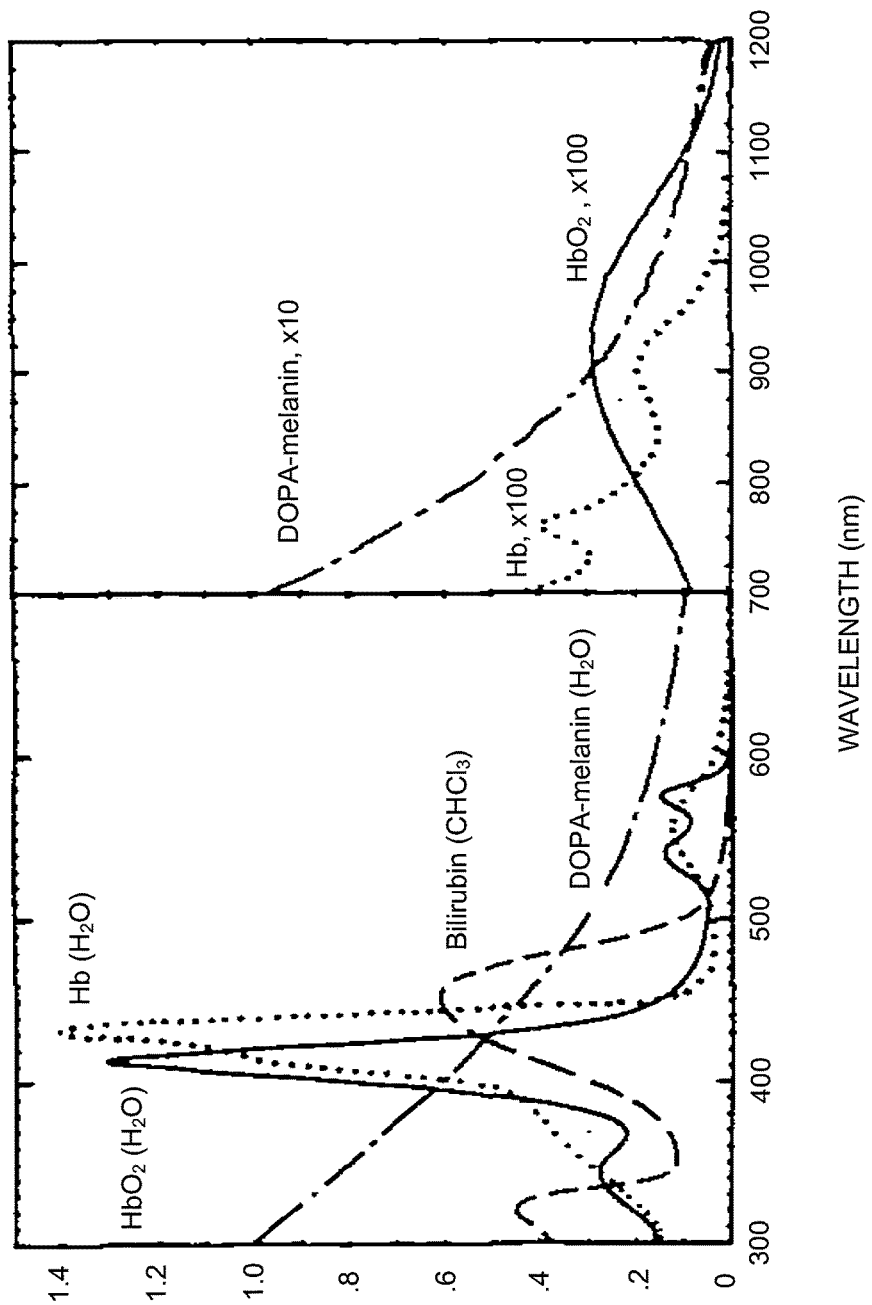
FIG. 1A shows the absorption spectra of the prominent chromophores of human skin.
Figure 1B:
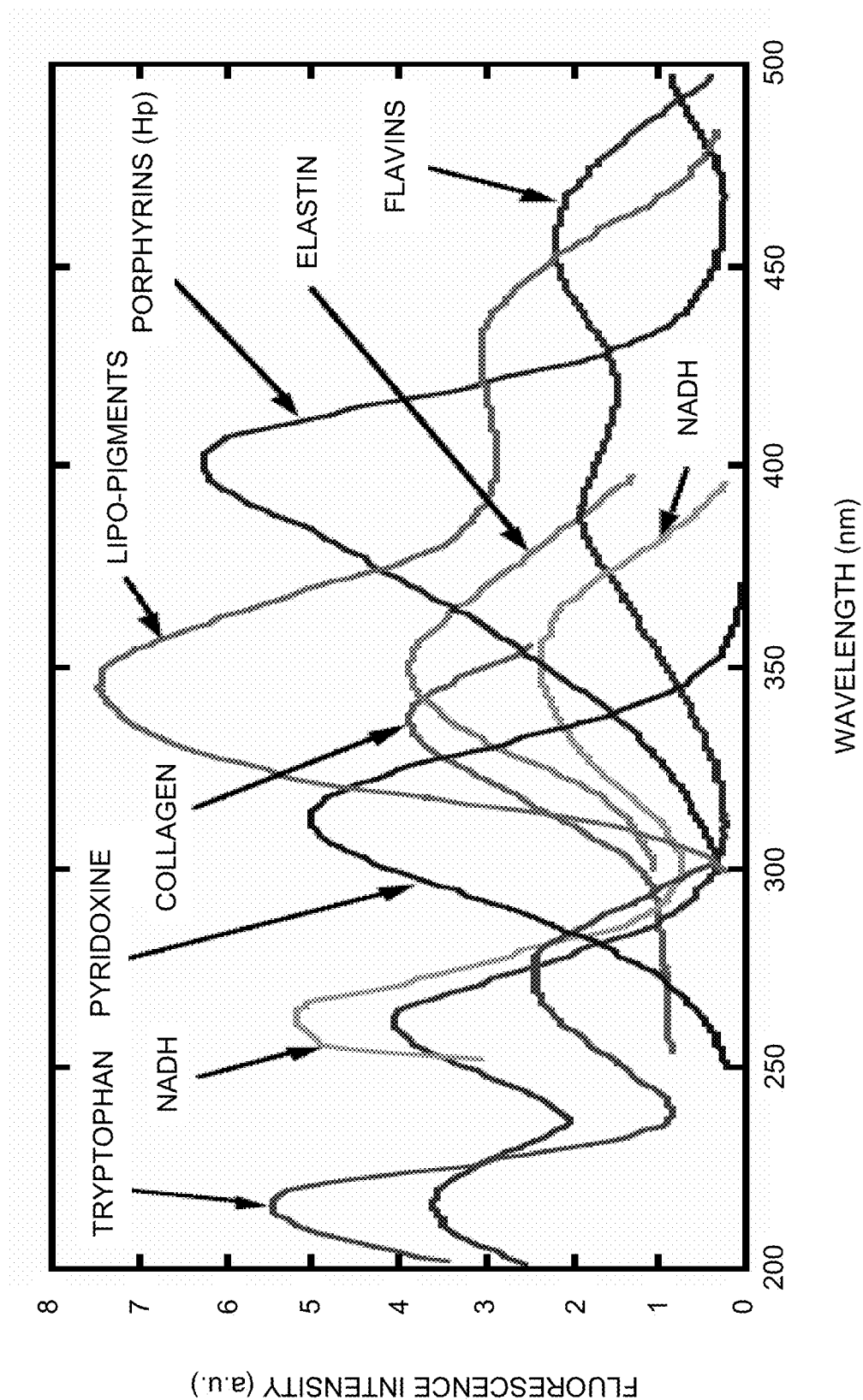
FIG. 1B shows the excitation/absorption spectra of the prominent endogenous fluorophores of human skin.
Figure 1C:
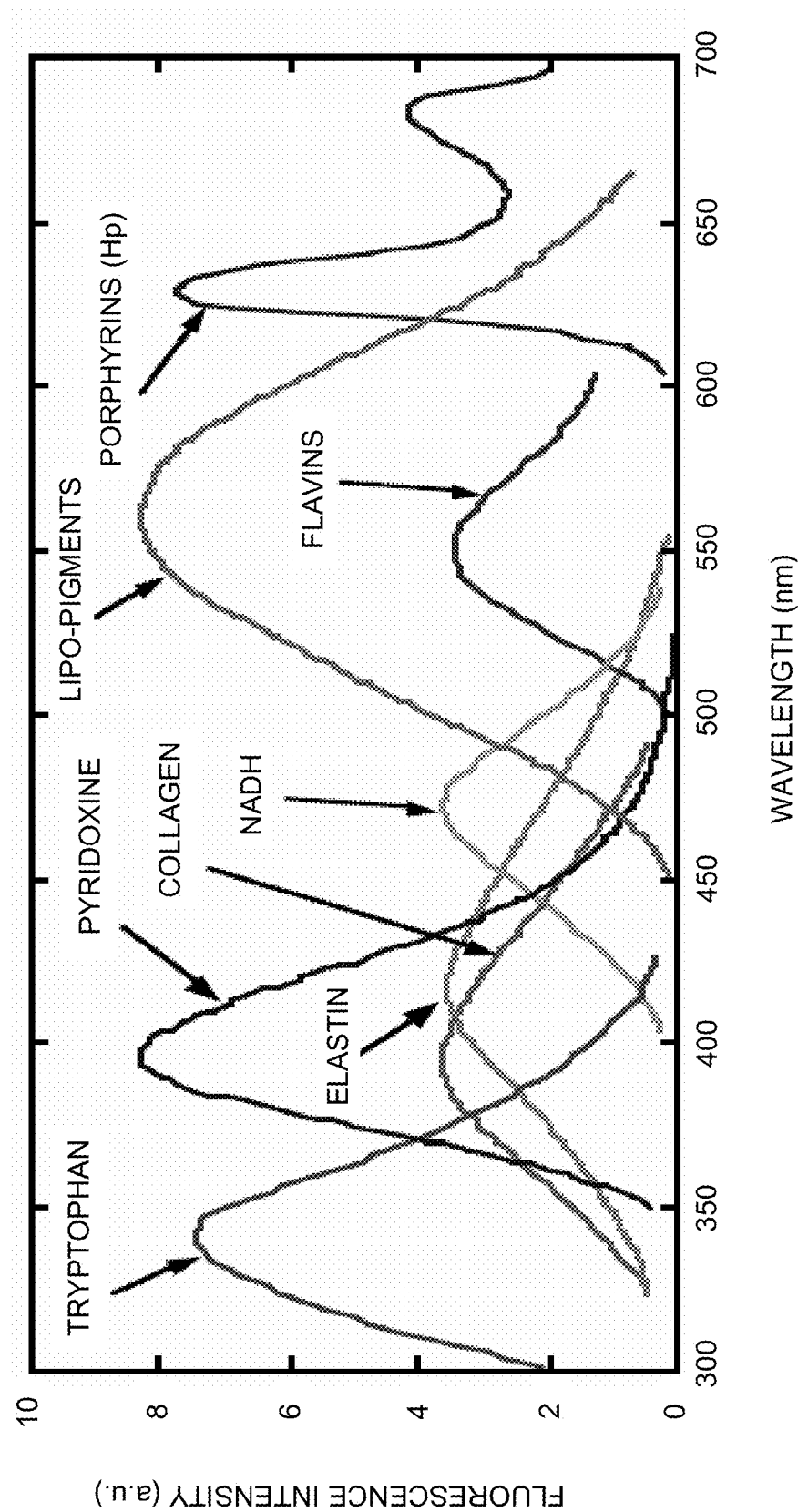
FIG. 1C shows the emission spectra of said endogenous fluorophores.

For measurements of other fluorophores (e.g., elastin, tryptophan, etc.), illumination at spectral wavelength bands centered around the fluorophores' respective maximum absorption peaks can be used. For example, with reference to FIG. 1B, tryptophan may be excited using illumination of a narrow spectral band of approximately 20 to 40 nm (FWHM) centered around 295 to 300 nm, and so on, for the other fluorophores. A trade-off of fluorescence signal-to-noise ratio of one fluorophore over another may be had by selecting a different illumination spectral band, depending on the imaging application.

In the exemplary method of FIG. 5, once the illumination wavelength band is selected at 510, the spectral band for capturing the image of a particular fluorophore's distribution is selected at 520, such as by selecting the appropriate filtering to insert in front of the image detector. Preferably, said band is selected so as to maximize detection of the fluorophore's fluorescence signal while suppressing signals from other sources, such as other fluorophores, the illumination source, and ambient light. For example, with excitation at 400 to 405 nm (FWHM±20 nm), porphyrin emits in the red to NIR spectral band (approximately 620 to 750 nm). Therefore, in order to capture the porphyrin fluorescence image, a long-pass detection filter with a cut-off wavelength of approximately 620 nm is preferred. A filter that will substantially transmit wavelengths from 500 to 600 nm is preferred for capturing horns fluorescence, and a filter that will substantially transmit wavelengths from 400 to 500 nm is preferred for capturing collagen fluorescence. Similar excitation and emission band correspondence may be used for imaging other fluorophores.

Once the appropriate illumination and detection bands are selected and set at 510 and 520, a fluorescence image of the subject tissue is captured at 530. Additionally, at 540, a corresponding excitation image is preferably captured in which the tissue is illuminated with the same spectral band illumination used in capturing (at 530) the corresponding fluorescence image. The excitation image comprises an image of the light reflected from the skin/tissue that is captured with no filter in the detection path, or using a suitable neutral density filter to match the input light levels. The excitation image is used in an image processing step 580, described below, to normalize the corresponding fluorescence image for non-uniform light distribution, heterogeneous absorption of light due to tissue chromophores, filter leakage, and/or ambient light distribution.

At 550, a determination is made as to whether there are more images to be captured using the same illumination used to capture the image at 530. If so, operation loops back to 520, new detection filtering is selected, and an additional image is captured at 530. If there are no more images to be captured with that illumination, operation proceeds to 560, where a determination is made as to whether images of all of the fluorophores of interest have been captured. If not, operation loops back to 510 and the above-described procedure is carried out for another fluorophore.

Once all fluorophores of interest have been imaged, as determined at 560, operation proceeds to 570 in which one or more dark-light images are captured in order to estimate the dark noise of the detector. The estimated dark noise image, or an average value of the dark noise, is subtracted from the fluorescence images in the image processing that is performed at 580. A dark-light image can be captured, for example, with the camera lens covered so that no light enters the camera, and it may be captured during every set of measurements or during a system calibration process. Multiple dark-light images would minimize the statistical error in the dark noise estimation.

At 580, the captured fluorescence images are processed. At 580, the captured fluorescence images are pre-processed. The pre-processing 580 may include at least some of the operations described above with respect to the pre-processing step 440 of the absorption image capture process of FIG. 4. As mentioned above, the dark noise of the detector may be estimated or measured and subtracted from the captured fluorescence and excitation data, as part of the pre-processing at 580.

Furthermore, while the fluorescence images/data can alone be used for further analysis, a differential measurement of fluorescence and excitation is preferred. The differential measurement, i.e., a ratio image, may be obtained at 580 by dividing or subtracting the fluorescence and excitation images (depending the image/data format), as follows:

$$\text{measurement} = (F*\text{fluorescence data})/(E*\text{excitation data}) \quad (1)$$

$$\text{measurement} = (F*\text{fluorescence data}) - (E*\text{excitation data}) \quad (2)$$

where F and E are constants accounting for variations in capture parameters. Preferably, the fluorescence and excitation data has been corrected for detector dark noise before this operation. A logarithm of the differential measurement may also be analyzed to obtain the fluorescence information, typically with a negative sign. Further, the fluorescence signal due to various fluorophores may be separated by using a similar differential measurement using two or more fluorescence images.

In an exemplary method of the present invention, chromophore distribution information may also be obtained from the fluorescence images. With proper selection of the illumination and detection spectral bands, the chromophore distribution information can be enhanced or suppressed. For suppressing the distribution information of a particular chromophore, spectral wavelengths for which absorption due to the chromophore is minimum may be used. On the other hand, the fluorescence that is emitted by the subject tissue may be used as a source of secondary illumination for capturing information about the tissue chromophore distributions. The spectral wavelengths for detection may be selected to enhance a specific chromophore absorption in the captured fluorescence image. Selecting a detection filter whose pass band is centered on the maximum absorption wavelength of a certain chromophore will provide a good contrast image of its distribution. For example, a proper choice of the detection spectral band between 500 and 600 nm will enhance the information about superficial blood vessels and/or oxy/deoxy-hemoglobin distribution in the captured fluorescence image. The hemoglobin information can be used, for example, to evaluate erythema. Similarly, a proper choice of the detection spectral band between 400 and 500 nm will enhance the information about melanin distribution in the captured fluorescence image.

Broad-Band Reflectance Imaging

Figure 6:
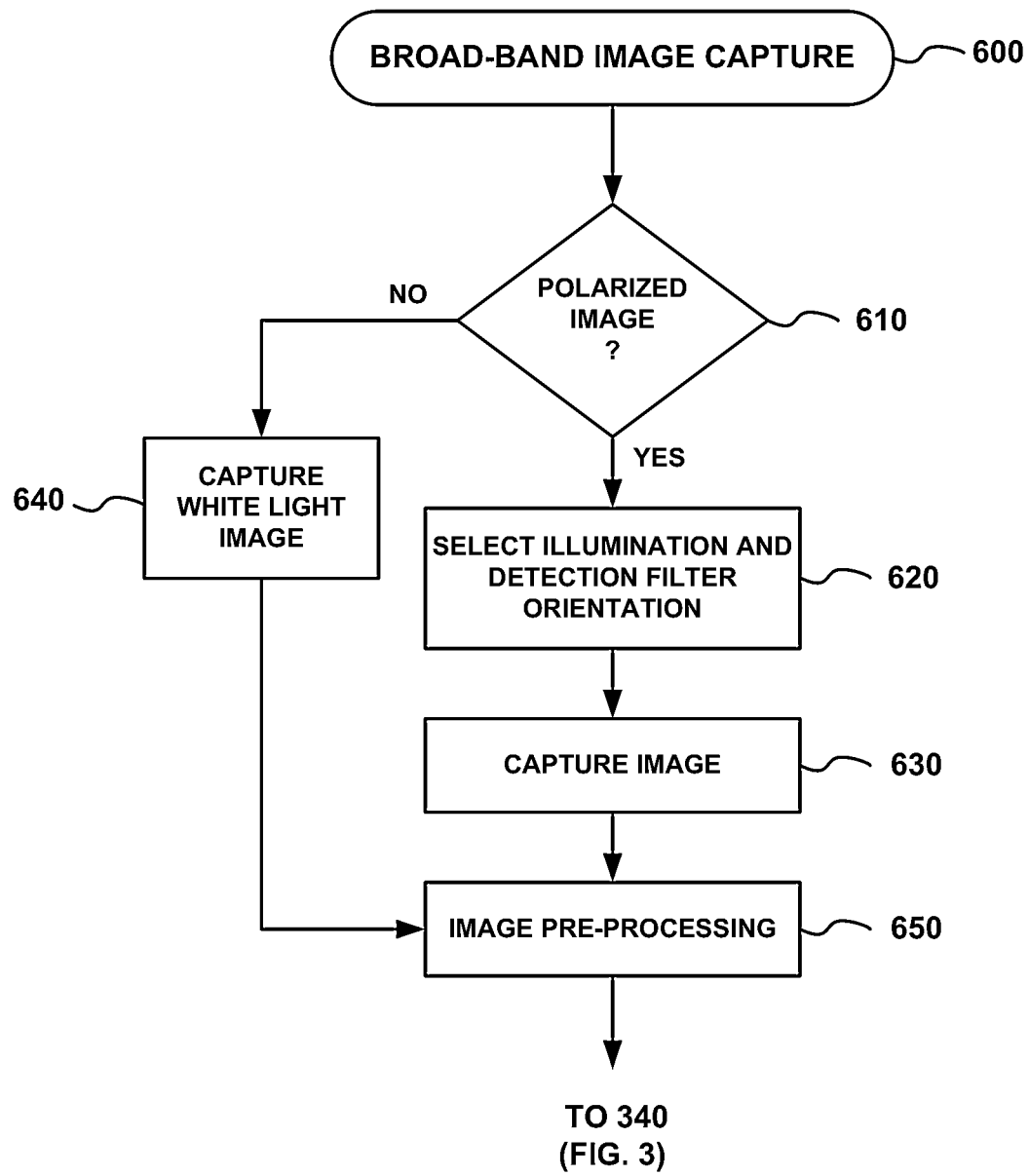
FIG. 6 is a flow chart depicting an exemplary broad-band illumination imaging method for identifying, characterizing, and measuring skin features of interest using standard (white) light illumination and polarized images.

FIG. 6 depicts an exemplary embodiment of a broad-band reflectance image capture process 600 in accordance with the present invention. Preferably, the image detector comprises a camera which captures a standard photograph of the subject tissue illuminated by one or more broad-band illumination sources that emit mainly visible light. Xenon flash source(s) with or without diffusing filters or fluorescent light source(s) may be used for this purpose. The light source(s) may be placed with respect to the camera so as to produce a uniform light distribution and/or a gradient light distribution that enhances skin features such as fine lines and wrinkles The apparatus of FIGS. 2A and 2B or other suitable apparatus can be used to carry out the process 600.

As shown in FIG. 6, at determination is made at 610 as to whether a polarized image is to be captured. If so, polarization filters for the illumination and detection paths are selected at 620. Parallel-polarized and cross-polarized images separate the tissue reflectance into surface reflectance and diffuse reflectance components, respectively. The parallel-polarized image is used to enhance surface characteristics, such as wrinkles, fine lines, pores, hair, scales, spots, etc. The cross-polarized image is used to enhance sub-surface characteristics, such as pigmentation, blood vessels, sub-surface hair, erythema, etc. Once the filters are selected, the image is captured at 630.

If it is determined at 610 that a non-polarized image is to be captured, an image with white light illumination is captured at 640.

At 650, image pre-processing is carried out, which may include at least some of the operations described above with respect to the pre-processing step 440 of the absorption image capture process of FIG. 4 as well as additional operations specific to the broad-band data captured in the process 600.

After pre-processing, operation proceeds to post-processing at 340, FIG. 3. In addition to the operations described above for the absorption and fluorescence imaging, post-processing 340 may include operations specific to the broad-band imaging of 600. For instance, the white light image captured with process 600 can be the main image that is presented to the system user, with the absorption and fluorescence images of processes 400 and 500 superimposed thereon.

Additionally, the white light and/or parallel polarized images may be analyzed using image processing and segmentation tools and techniques to obtain topology and surface features and landmarks, such as the tip of the nose, lips, and eyes, among others.

Furthermore, the cross-polarized image can be transformed to a pre-defined color space that provides optimal separation between red pigmentation (for hemoglobin) and brown pigmentation (for melanin) These Red and Brown images can be further analyzed and/or presented. Further, for Acne lesion classification, the Red image can be used in differentiating a papule from a pustule (a lesion with pus). Lesions with pus will be highlighted in the Red image as white spots because the light absorption of pus is significantly different from hemoglobin.

Feature Detection, Classification, Analysis, and Evaluation

In the exemplary method of the present invention shown in FIG. 3, after post-processing 340, the individual multi-spectral images and/or any combination of these images can be analyzed at 350 to evaluate the subject tissue's characteristics. The entire image or an area of interest in the acquired image may be analyzed for this purpose. The analysis may be used for the classification or detection of a certain pathology and/or skin feature, including, for example, classifying acne lesions, assessing the severity of acne lesions, providing a score value in comparison to a database, comparing images captured at different time points, evaluating progression of the disease, recommending a cosmetic or medical treatment procedure, tracking product effectiveness, and/or monitoring treatment effectiveness.

In an exemplary method of the present invention, the horns and/or porphyrin fluorescence images are processed at 350 to detect pores, P. acnes bacteria-related activity, and to detect and classify open and closed comedons. The horns fluorescence image generated by the process 320 is also processed at 350 to detect dark rings around lesions. Such dark rings signify hemoglobin absorption which can be used for classifying inflammatory and non-inflammatory acne lesions. Similar information may also be obtained from 2D/3D hemoglobin absorption maps generated by the process 310. Furthermore, the horns and/or porphyrin fluorescent spots detected may be used to predict possible acne lesion sites. Craters and mounds may be detected in the collagen fluorescence image and this information may be used for improving the accuracy of lesion classification. The polarized image and/or the white light image generated by the process 330 may be processed for obtaining topological characteristics as well as for improving the accuracy of lesion classification.

In an exemplary method of the present invention, collagen fluorescence images can be processed using line/edge detection techniques to identify wrinkles and fine lines. The polarized and/or white light image(s) may be similarly processed and the combined information may be used to improve detection accuracy.

Image processing including image feature detection, rescaling, noise removal, enhancement, and pseudo coloring, can be performed using known techniques. Image processing techniques used may also include those described in U.S. Provisional Patent Application No. 60/951,313 entitled "Method and Apparatus for Realistic Simulation of Wrinkle Aging" and U.S. patent application Ser. No. 11/681,509 entitled "Method and Apparatus for Simulation of Facial Skin Aging and De-aging," both of which are incorporated herein by reference in their entireties.

Unless defined otherwise, all technical and scientific terms used herein have the same meaning as commonly understood by one of ordinary skill in the art to which the invention belongs.

All patents and patent applications referred to herein are incorporated by reference in their entirety.

It is understood that the above-described embodiments are illustrative of only a few of the possible applications of the present invention. Numerous and varied other arrangements can be made by those skilled in the art without departing from the spirit and scope of the present invention.

REFERENCES

[1]. V. Ntziachristos, Fluorescence Molecular Imaging, Annu. Rev. Biomed. Eng., 8, 1-33, 2006.

[2]. N. Kollias and G. N. Stamatas, Optical Non-Invasive Approaches to Diagnosis of Skin Diseases, Optical Diagnostics In Dermatology, 7(1), 64-75, 2002.

[3]. Zaheer A, Lenkinski R E, Mahmood A, et al., In vivo near-infrared fluorescence imaging of osteobllastic activity, Nat. Biotechnol., 19, 1148-1154, 2001.

[4]. Tung C H, Fluorescent peptide probes for in vivo diagnostic imaging, Biopolymers 76, 391-403, 2004.

[5]. Muguruma N, et al., Antibodies labeled with Fluorescence-agent excitable by infrared rays, J. Gastroenterol. 33, 467-471, 1998.

[6]. Weissleder R, Tung C H, Mahmood U, et al., In vivo imaging of tumors with protease-activated near-infrared fluorescent probes, Nat. Biotechnol., 17, 375-378, 1999.

[7]. Tung C H, Mahmood U, Bredow S, et al., In vivo imaging of proteolytic enzyme activity using a novel molecular reporter, Cancer Res., 60, 4953-4958, 2000.

[8]. Bogdanov A A Jr., Lin C P, Simonova M, et al., Cellular activation of the self-quenched fluorescent reporter probe in tumor microenvironment, Neoplasia, 4, 228-236, 2002

[9]. J. Hewett, V. Nadeau, J. Ferguson, H. Moseley, et al., Application of a compact multispectral imaging system with integrated excitation source to in vivo monitoring of fluorescence during topical photodynamic therapy of superficial skin cancers, Photochem. and Photobiol., March 2001.

[10]. Yang M, Baranov E, Jinag P, et al., Whole-body optical imaging of green fluorescent protin-expressing tumors and metastases, Proc. Natl. Acad. Sci., USA 97, 1206-1211, 2000.

[11]. Ito S, et al., Detection of human gastric cancer in resected specimens using a novel infrared fluorescent anti human carcinoembryonic antigen antibody with an infrared fluorescence endoscope in vitro, Endoscopy, 33, 849-853, 2001.

[12]. Richards-Kortum R, Sevick-Muraca E, Quantitative optical spectroscopy for tissue diagnosis, Annu. Rev. Physical. Chem., 47, 555-606, 1996.

[13]. Wang T D, et al., In vivo identification of colonic dysplasia using fluorescence endoscopic imaging, Gastrointest. Endosc. 49, 447-455, 1999.

[14]. Mahmood U, Tung C, Bagdanov A Jr., et al., Near-infrared optical imaging of protease activity for tumor detection, Radiology 213, 866-870, 1999.

[15]. S. V. Patwardhan, S. Bloch, S. Achilefu, and J. Culver, Time-dependent whole-body fluorescence tomography of probe bio-distributions in mice, Optics Express, 13(7), 2564-2577, 2005.

[16]. Edwards E A, and Duntley S Q, The pigment and color of human skin, Am. J. Anat., 65, 1-33, 1939.

[17]. Anderson R R, and Parrish J A, The optics of human skin, J. Invest. Dermatol. 77, 13-19, 1981.

[18]. M. Van Gemert, Jacques S L, Sterenborg H, Star W M, Skin optics, IEEE Trans. Biomed. Eng., 36, 1146-1154, 1989.

[19]. Graaff R, Dassel A C M, Koelink M H, de Mul F F M, Aarnoudse J G, Zijlstra W G, Optical properties of human dermis in vitro and in vivo, Appl. Opt., 32, 435-447, 1993.

[20]. W. Bruls and J. van der Leun, Forward Scattering Properties of Human Epidermal Layers, Photochem. Photobiol., 40, 231-242, 1984.

[21]. S. Jacques, Skin Optics Summary, Oregon Medical Laser Center News, January 1998. http://omlc.bme.o-gi.edu/news/jan98/skinoptics.html

[22]. W. Cui, L. Ostrander and B. Lee, In Vivo Reflectance of Blood and Tissue as a Function of Light Wavelength, IEEE Trans. Biomed. Eng., 37(6), 632-639, 1990.

[23]. S. Jacques, C. Alter and S. Prahl, Angular Dependence of He—Ne Laser Light Scattering by Human Dermis, Laser Life Sci., 1, 309-333, 1987.

[24]. S. R. Arridge, Optical tomography in medical imaging, Inverse Problems, 15(2), R41-R93, 1999.

[25]. J. P. Culver, R. Choe, M. J. Holboke, L. Zubkov, T. Durduran, A. Slemp, V. Ntziachristos, D. N. Pattanayak, B. Chance, and A. G. Yodh, Three-dimensional diffuse optical tomography in the parallel plane transmission geometry: evaluation of a hybrid frequency domain/continuous wave clinical system for breast imaging, Med. Phys., 30, 235-247, 2003.

[26]. J. P. Culver, T. Durduran, D. Furuya, C. Cheung, J. H. Greenberg, and A. G. Yodh, Diffuse optical tomography of cerebral blood flow, oxygenation and metabolism in rat during focal ischemia, J. Cereb. Blood Flow Metab., 23, 911-924, 2003.

[27]. B. Chance, M. T. Dait, C. Zhang, T. Hamaoka, and F. Hagerman, Recovery from exercise-induced desaturation in the quadriceps muscles of elite competitive rowers, Am. J. Physiol., 262, C766-C775, 1992.

[28]. R. Belardinelli, T. J. Barstow, J. Porszasz, and K. Wasserman, Skeletal muscle oxygenation during constant work rate exercise, Med. Sci. Sports Exercise, 27, 512-519 1995.

[29]. H. Wang, M. E. Putt, M. J. Emanuele, D. B. Shin, E. Glatstein, A. G. Yodh, and T. M. Busch, Treatment-induced changes in tumor oxygenation predict photodynamic therapy outcome, Cancer Res., 64, 7553-7561, 2004.

[30]. S. V. Patwardhan and Joseph P. Culver, Quantitative Diffuse Optical Tomography for Small Animals Using an Ultra-fast Gated Image Intensifier, Journal of Biomed. Optics, 13(1), 2008.

[31]. N Iftimia, H B Jiang, Quantitative optical image reconstruction of turbid media by use of direct-current measurements, Appl. Opt. 39, 5256-5261, 2000.

[32]. Mustakallio K K, Korhonen P, Monochromatic ultraviolet-photography in dermatology, J. Invest. Dermatol., 47, 351-356, 1966.

[33]. Fulton J E, Utilizing the ultraviolet (UV-detect) camera to enhance the appearance of photodamage and other skin conditions, Dermatol. Surg., 23, 163-169, 1997

[34]. Pagnoni A, Kligman A M, Kollias N, Goldberg S, Stoudemayer T, Digital fluorescence photography can assess the suppressive elect of benzoyl peroxide on *Propionibacterium acnes*, J. Am. Acad. Dermatol., 41(1), 710-716, 1999.

[35]. Lucchina L C, Kollias N, Gillies R, et al, Fluorescence photography in the evaluation of acne, J. Am. Acad. Dermatol., 35, 58-63, 1996.

[36]. Phillips S B, Kollias N, Gillies R, Muccini J A, Drake L A, Polarized light photography enhances visualization of inflammatory lesions of acne vulgaris, J. Am. Acad. Dermatol., 37, 948-952, 1997.

[37]. Anderson R R, Polarized light examination and photography of the skin, Arch. Dermatol., 127, 1000-1005, 1991.

[38]. S. V. Patwardhan and J. P. Culver. High-Frequency, ICCD Diffuse Optical Tomography System for Separation of Optical Properties in Small Tissue Volumes in Biomedical Optics 2006 Technical Digest. 2006: Optical Society of America, Washington, D.C., 2006.

[39]. S. Bjoern, S. V. Patwardhan and J. P. Culver. The Influence of Hetergeneous Optical Properties on Fluorescence Diffusion Tomography of Small Animals in Biomedical Optics 2006 Technical Digest. Optical Society of America, Washington, D.C., 2006.

[40]. H Dehghani, B A Brooksby, B W Pogue, and K D Paulsen, Effects of refractive index on near-infrared tomography of the breast, Applied Optics, 44(10), 870-1878, 2005.

[41]. B W Zeff, B R White, H D, B L Schlaggar, and J P Culver, Retinotopic mapping of adult human visual cortex with high-density diffuse optical tomography, Published online before print Jul. 6, 2007, 10.1073/pnas.0611266104.

[42]. S. Maganti and A. P. Dhawan, "3-D Nevoscope image reconstruction using diverging ray ART", Proceedings SPIE International Conference on Biomedical Optics, 1997.

[43]. S. V. Patwardhan et al., Monte Carlo simulation of light-tissue interaction: three-dimensional simulation for trans-illumination-based imaging of skin lesions, IEEE Trans. Biomed. Engg. 52(7), 1227-1236, 2005.

[44]. N. Tsumura, H. Haneishi, and, Y. Miyake, Independent component analysis of skin color image, The 6th Color Imaging Conference: Color Science, Systems and Applications, vol. (6), Scottsdale, Ariz., 1998.

[45]. S. Cotton, and, E. Claridge, Developing a Predictive Model of Human Skin Coloring, Proc. SPIE Medical Imagining, 2708, 814-825, 1996

[46]. J. W. Feather, D. J. Ellis, and, G. Leslie, A portable reflectometer for the rapid quantification of cutaneous haemoglobin and melanin, Phys. Med. Biol., 33(6), 711-723, 1988.

[47]. Takiwaki H., Measurement of skin color: practical application and theoretical considerations, J. Med. Invest., 44(3-4), 121-126, 1998.

[48]. Japanese Patent JP 3365227: Measuring methods and device of optical properties of surface condition of skin, K Haruhito, N. Yoshinao and, Y. Yukihiro, May 19, 1998.

[49]. Anderson R R, Parrish J A: The optics of human skin. J Invest Dermatol., 77, 13-19, 1981.

What is claimed is:

1. A method of imaging human skin in vivo comprising:
obtaining a fluorescence image of the human skin;
obtaining a cross-polarized broadband white light reflectance image of the human skin;
processing the cross-polarized broadband white light reflectance image to obtain a chromophore distribution image; and
generating a normalized fluorescence image by normalizing the fluorescence image using the chromophore distribution image.

2. The method of claim 1, wherein processing the cross-polarized broadband white light reflectance image includes at least one of an Independent Component Analysis (ICA) and a Principle Component Analysis (PCA).

3. The method of claim 1 wherein obtaining the fluorescence image includes capturing the fluorescence image including filtering light reflected from the human skin to eliminate at least one of an ultraviolet and an infrared light.

4. The method of claim 1, wherein the chromophore distribution image includes a distribution of at least one chromophore selected from the group consisting of hemoglobin, melanin and bilirubin.

5. The method of claim 1 comprising:
storing at least one of the fluorescence image, the normalized fluorescence image, the cross-polarized broadband white light reflectance image and the chromophore distribution image; and
displaying at least one of the fluorescence image, the cross-polarized broadband white light reflectance image and the chromophore distribution image.

6. The method of claim 1 comprising identifying a skin pathological condition selected from the group consisting of rosacea, hyper-pigmentation, ultraviolet light damage, melanin spots, nevi, sun tan, erythema, inflammation, irritation, and skin lesion.

7. The method of claim 1 comprising:
using at least one of the fluorescence image, the normalized fluorescence image, the chromophore distribution image, and the cross-polarized broadband white light reflectance image for:
identifying scars and spots,
classifying inflammatory from non-inflammatory lesions,
evaluating erythema by analyzing hemoglobin information,
detecting wrinkles,
predicting future wrinkle development,
evaluating skin hydration levels using water absorption information,
evaluating at least one of a normal, dysplastic, and malignant skin lesion,
classifying at least one of a normal, dysplastic, and malignant lesion,
evaluating at least one of a skin pathology including rosacea, hyper-pigmentation, skin burn, irritation, and inflammation,
classifying an acne lesion as being of a type including at least one of an open comedone, closed comedone, papule, pustule, nodule, cyst, burnt-out lesion, and excoriated lesion,
predicting future acne lesion formation sites,
evaluating at least one of a treatment product and a treatment procedure; or
recommending at least one of a treatment product and a treatment procedure.

8. The method of claim 1 comprising processing the normalized fluorescence image so as to characterize a condition of the human skin.

9. The method of claim 8 comprising at least one of:
communicating at least one of the normalized fluorescence image and the processed normalized fluorescence image;
storing at least one of the normalized fluorescence image and the processed normalized fluorescence image; and
displaying at least one of the normalized fluorescence image and the processed normalized fluorescence image.

10. The method of claim 1, wherein obtaining the fluorescence image includes:
illuminating the human skin with a narrow spectral band illumination which excites a plurality of endogenous fluorophores including an endogenous target fluorophore of the human skin to each generate an emission signal;
filtering the emission signals so as to pass the emission signal of the target fluorophore while suppressing emissions from at least one other source;
capturing an image of the human skin by detecting the filtered emission signals;
capturing an excitation image so as to characterize a light distribution over a surface of the human skin by detecting light reflected from the human skin; and
normalizing the captured image using the excitation image thereby yielding the fluorescence image,
wherein the narrow spectral band illumination and the filtering are selected so that the filtered emission signal of the target fluorophore can be individually detected among the filtered emission signals.

11. The method of claim 10, wherein a wavelength range of the narrow spectral band illumination is selected so as to optimally excite the target fluorophore.

12. The method of claim 10, wherein the at least one other source includes at least one of a further fluorophore, an ambient light source, and an excitation light source.

13. The method of claim 10, wherein:
the narrow spectral band illumination is centered around 405 nm (±15 nm), and
the filtering is performed with at least one of:
a 10 to 50 nm (FWHM) narrow band-pass filter centered around 460 nm (±20 nm), for detecting a collagen fluorescence signal,
a 10 to 50 nm (FWHM) narrow band-pass filter centered around 560 nm (±20 nm), for detecting a horns fluorescence signal, and
a long-pass filter with a cut-off wavelength of approximately 620 nm for detecting a porphyrin fluorescence signal.

14. The method of claim 10, wherein:
the narrow spectral band illumination is centered around 350 nm (±15 nm),
the target fluorophore includes elastin, and
the filtering is performed with a 10 to 50 nm (FWHM) narrow band-pass filter centered around 410 nm (±20 nm).

15. The method of claim 1, wherein normalizing the fluorescence image using the chromophore distribution image includes compensating for loss of at least one of an excitation and emission signal.

16. An apparatus for imaging human skin in vivo comprising:
a storage device for storing instructions; and
a processor configured to execute the instructions to:
obtain a fluorescence image of the human skin;
obtain a cross-polarized broadband white light reflectance image of the human skin;
process the cross-polarized broadband white light reflectance image to obtain a chromophore distribution image; and
generate a normalized fluorescence image by normalizing the fluorescence image using the chromophore distribution image.

17. The apparatus of claim 16, wherein processing the cross-polarized broadband white light reflectance image includes at least one of an Independent Component Analysis (ICA) and a Principle Component Analysis (PCA).

18. The apparatus of claim 16, wherein the chromophore distribution image includes a distribution of at least one chromophore selected from the group consisting of hemoglobin, melanin and bilirubin.

19. The apparatus of claim 16, wherein the processor is configured to execute the instructions to process the normalized fluorescence image so as to characterize a condition of the human skin.

20. The apparatus of claim 16, wherein the processor is configured to execute the instructions to obtain the fluorescence image by:
controlling an image capture device to capture an image of the human skin, the human skin having been illuminated with a narrow spectral band illumination which excites a plurality of endogenous fluorophores including an endogenous target fluorophore of the human skin to each generate an emission signal, the emission signals having been filtered so as to pass the emission signal of the target fluorophore while suppressing emissions from at least one other source, and the image having been captured by detecting the filtered emission signals, wherein the narrow spectral band illumination and the filtering have been selected so that the filtered emission signal of the target fluorophore can be individually detected among the filtered emission signals;
controlling the image capture device to capture an excitation image that has been captured by detecting light reflected from the human skin so as to characterize a light distribution over the human skin; and
normalizing the captured image using the excitation image to thereby yield the fluorescence image.

21. The apparatus of claim 20, wherein:
the narrow spectral band illumination is centered around 405 nm (±15 nm), and
the filtering is performed with at least one of:
a 10 to 50 nm (FWHM) narrow band-pass filter centered around 460 nm (±20 nm), for detecting a collagen fluorescence signal,
a 10 to 50 nm (FWHM) narrow band-pass filter centered around 560 nm (±20 nm), for detecting a horns fluorescence signal, and
a long-pass filter with a cut-off wavelength of approximately 620 nm for detecting a porphyrin fluorescence signal.

22. The apparatus of claim 16, wherein normalizing the fluorescence image using the chromophore distribution image includes compensating for loss of at least one of an excitation and emission signal.

* * * * *